US011730631B2

(12) United States Patent
Rehbein et al.

(10) Patent No.: US 11,730,631 B2
(45) Date of Patent: Aug. 22, 2023

(54) CONTOURED FOAM DRESSING SHAPED FOR PROVIDING NEGATIVE PRESSURE TO INCISIONS IN THE BREAST

(71) Applicant: KCI LICENSING, INC., San Antonio, TX (US)

(72) Inventors: Jonathan G. Rehbein, San Antonio, TX (US); Richard Kazala, San Antonio, TX (US); Enrique L. Sandoval, Fair Oaks Ranch, TX (US); Larry Tab Randolph, San Antonio, TX (US); Luke Perkins, San Antonio, TX (US); Ronald P. Silverman, Pikesville, MD (US)

(73) Assignee: KCI Licensing, Inc., San Antonio, TX (US)

( * ) Notice: Subject to any disclaimer, the term of this patent is extended or adjusted under 35 U.S.C. 154(b) by 671 days.

(21) Appl. No.: 16/156,387

(22) Filed: Oct. 10, 2018

(65) Prior Publication Data
US 2019/0125590 A1    May 2, 2019

Related U.S. Application Data

(60) Provisional application No. 62/578,173, filed on Oct. 27, 2017.

(51) Int. Cl.
*A61F 13/14*    (2006.01)
*A61F 13/02*    (2006.01)
(Continued)

(52) U.S. Cl.
CPC ........ *A61F 13/14* (2013.01); *A61F 13/00068* (2013.01); *A61F 13/0216* (2013.01);
(Continued)

(58) Field of Classification Search
CPC .............. A61F 13/00068; A61F 13/145; A61F 2013/15016; A61F 5/03; A61F 2007/0021;
(Continued)

(56) References Cited

U.S. PATENT DOCUMENTS 1,355,846 A    10/1920    Rannells
2,547,758 A    4/1951    Keeling
(Continued)

FOREIGN PATENT DOCUMENTS

AU        550575 B2    3/1986
AU        745271 B2    3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Adam Marcetich
*Assistant Examiner* — Meagan Ngo

(57)    ABSTRACT

A negative pressure wound dressing for use with breast incisions. The wound dressing includes a drape layer, a manifold layer, a base layer, and a reduced pressure interface. The drape layer has a first surface and a second, wound-facing, surface. The drape layer is substantially impermeable to liquid and substantially permeable to vapor. The manifold layer has a first surface and a second, wound-facing surface. The manifold layer has a perimeter defined by a first convex curved side surface defining a first lobe, a second convex curved side surface defining a second lobe, and a connecting portion between the first lobe and the second lobe. The base layer is configured to: (i) couple the
(Continued)

drape layer to the manifold layer, and (ii) the dressing to a patient's tissue. The reduced pressure interface is integrated with the drape layer.

14 Claims, 11 Drawing Sheets

(51) Int. Cl.
  *A61M 1/00* (2006.01)
  *A61F 13/00* (2006.01)
(52) U.S. Cl.
  CPC ........... *A61F 13/145* (2013.01); *A61M 1/915* (2021.05); *A61M 1/962* (2021.05); *A61F 2013/0028* (2013.01); *A61F 2013/00182* (2013.01); *A61M 1/917* (2021.05); *A61M 2210/1007* (2013.01)
(58) Field of Classification Search
  CPC ...... A61F 13/14–148; A61F 2007/0019–0021; A61F 2013/00804
  See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 8,100,848 B2 | 1/2012 | Wilkes et al. |
| 8,129,580 B2 | 3/2012 | Wilkes et al. |
| 8,715,253 B2 | 5/2014 | Cavanaugh et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2008/0249457 A1 | 10/2008 | Li et al. |
| 2009/0234306 A1* | 9/2009 | Vitaris ................ A61F 13/0216 604/304 |
| 2009/0293887 A1* | 12/2009 | Wilkes .............. A61F 13/00017 128/888 |
| 2012/0330253 A1* | 12/2012 | Robinson ............ A61F 13/0216 604/319 |
| 2013/0102983 A1* | 4/2013 | Gilmartin ............. A61F 13/141 604/372 |
| 2014/0350494 A1* | 11/2014 | Hartwell ........... A61F 13/00068 604/319 |
| 2015/0032035 A1* | 1/2015 | Banwell ............ A61F 13/00068 601/6 |
| 2019/0290499 A1* | 9/2019 | Askem .................... A61M 1/90 |
| 2020/0138632 A1 | 5/2020 | Holm et al. |

FOREIGN PATENT DOCUMENTS

| | | |
|---|---|---|
| AU | 755496 B2 | 12/2002 |
| CA | 2005436 A1 | 6/1990 |
| CN | 102065809 A | 5/2011 |
| CN | 202184857 U | 4/2012 |

(56) References Cited

FOREIGN PATENT DOCUMENTS

| | | |
|---|---|---|
| CN | 105246439 A | 1/2016 |
| CN | 107252383 A | 10/2017 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| JP | 2015-144844 | 8/2015 |
| JP | 2017-148527 | 8/2017 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2009/146441 A1 | 12/2009 |
| WO | 2010068502 A1 | 6/2010 |
| WO | 2011087871 A2 | 7/2011 |
| WO | WO-2013/007973 A2 | 1/2013 |
| WO | WO-2017/148824 A1 | 9/2017 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds" Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax"Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract,

(56) References Cited

OTHER PUBLICATIONS editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Anonymous,"3M Tegaderm Transparent Film Dressings—Product Profile", http://multimedia.3m.com/mws/media/447983O/tegaderm-transparent-film-dressing-brochure.pdf, Jan. 1, 2012, pp. 1-8 (p. 3).
International Search Report & Written Opinion in International Application No. PCT/US2018/055182, dated Feb. 28, 2019 (26 pages).
Japanese Notice of Rejection for Corresponding Application No. 2020-523355, dated Mar. 29, 2022.
Chinese Third Office Action Corresponding to Application No. 2018800687710, dated Aug. 10, 2022.

\* cited by examiner

CONTOURED FOAM DRESSING SHAPED FOR PROVIDING NEGATIVE PRESSURE TO INCISIONS IN THE BREAST

CROSS-REFERENCE TO RELATED APPLICATIONS

The present application claims the benefit of and priority to U.S. Provisional Patent Application No. 62/578,173, filed Oct. 27, 2017, the entire contents of which are incorporated herein by reference.

BACKGROUND

The present disclosure relates generally to a wound therapy system, and more particularly to a wound therapy system contoured to provide negative pressure wound therapy to the site of a breast incision.

Negative pressure wound therapy (NPWT) is a type of wound therapy that involves applying a negative pressure to a wound site to promote wound healing. NPWT can be used to treat wounds in the breast area caused by mastectomies, breast enhancement surgery, breast reconstruction surgery, or breast reduction surgery. Current negative pressure dressings used to treat the breast area are generally shaped in the form of a brassiere and include a first cup and a second cup made from a dressing material connected by a band of material. Such dressings must usually be provided in many sizes and, in the case of mastectomies, may require the use of a prosthetic device in one or both of the cups.

Recent developments in NPWT therapy include the use of adhesive wound dressings that can be positioned over a wound to treat the wound and the surrounding area. However, existing adhesive NPWT dressings are primarily linear dressings designed to treat linear wounds. In most instances, breast surgeries involve two generally perpendicular incisions. A first incision is a generally horizontal incision proximate a base of the breast and a second incision is generally perpendicular to the first incision and extends upward from the first incision and around a top of the nipple. The two incisions form an inverted T-shape. The existing NPWT dressings are configured to treat one of the first incision and the second incision, and must be customized to treat the specific incision pattern, breast size, and/or left breast or right breast of the patient.

SUMMARY

One implementation of the present disclosure is a negative pressure wound therapy system for use with breast incisions. The system includes a wound dressing including a drape layer, a manifold layer, a reduced-pressure interface, a base layer, and an optional wound-interface layer. The drape layer is configured to provide a sealed space over a wound or incision, and has a first surface and a second, wound-facing, surface. The drape layer is substantially impermeable to liquid and substantially permeable to vapor. The manifold layer allows for the transmission of negative pressure to a patient's tissue, and has a first surface and a second, wound-facing surface. In some embodiments, the manifold layer is comprised of a hydrophobic foam, such as an open-cell polyurethane foam. The manifold layer has a perimeter defined by a first convex curved side surface defining a first lobe, a second convex curved side surface defining a second lobe, and a connecting portion between the first lobe and the second lobe. The reduced-pressure interface allows for the fluid communication of negative pressure from a negative pressure source into the dressing (through the drape layer), via a conduit configured to fluidly couple the negative pressure source and the reduced-pressure interface. The reduced-pressure interface is preferably integrated with the drape layer; though alternatively, it can be separate from the drape layer and configured to be coupled to the drape layer by a user. The base layer may comprise polyurethane film coated with an adhesive (such as acrylic or silicone adhesive) on both sides. The base layer may be (i) configured to secure the drape layer to the manifold layer and, if present, the wound-interface layer, and (ii) configured to secure the dressing to a patient's tissue. In some embodiments, the functionality of the base layer is provided by the drape layer, and a separate base layer is not included. In some embodiments, the wound-facing side of the base layer includes a hydrocolloid adhesive. The optional wound interface layer may comprise a wicking material, and may optionally include antimicrobials (such as silver).

Another implementation of the present disclosure is a negative pressure wound dressing for use with breast incisions. The wound dressing includes a drape layer, a manifold layer, a base layer, and a reduced pressure interface. The drape layer has a first surface and a second, wound-facing, surface. The drape layer is substantially impermeable to liquid and substantially permeable to vapor. The manifold layer has a first surface and a second, wound-facing surface. The manifold layer has a perimeter defined by a first convex curved side surface defining a first lobe, a second convex curved side surface defining a second lobe, and a connecting portion between the first lobe and the second lobe. The base layer is (i) configured to secure the drape layer to the manifold layer, and (ii) configured to secure the dressing to a patient's tissue. The reduced pressure interface is integrated with the drape layer.

Another implementation of the present disclosure is a wound dressing for negative pressure wound therapy treatment of breast incisions including a manifold layer and a drape layer that is substantially impermeable to liquid and substantially permeable to vapor. The manifold layer includes a first surface, a second, wound-facing, surface, and a plurality of scores formed in the first surface and extending towards the second surface. The plurality of scores define a geometric scoring pattern. The manifold layer is bendable about the plurality of scores.

Another implementation of the present disclosure is a negative pressure wound dressing for use with breast incisions. The wound dressing includes a drape layer, a manifold layer, a base layer, and a reduced-pressure interface. The drape layer has a first surface and a second, wound-facing, surface. The drape layer is substantially impermeable to liquid and substantially permeable to vapor. The manifold layer has a first surface and a second, wound-facing surface. The manifold layer includes a perimeter defined by a first curved corner having first radius of curvature, a second curved corner having a second radius of curvature, and a third curved corner having a third radius of curvature. The third radius of curvature is smaller than the first radius of curvature and the second radius of curvature. The base layer is (i) configured to secure the drape layer to the manifold layer and (ii) configured to secure the wound dressing to a patient's tissue. The reduced-pressure interface is integrated with the drape layer.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Figure 1:
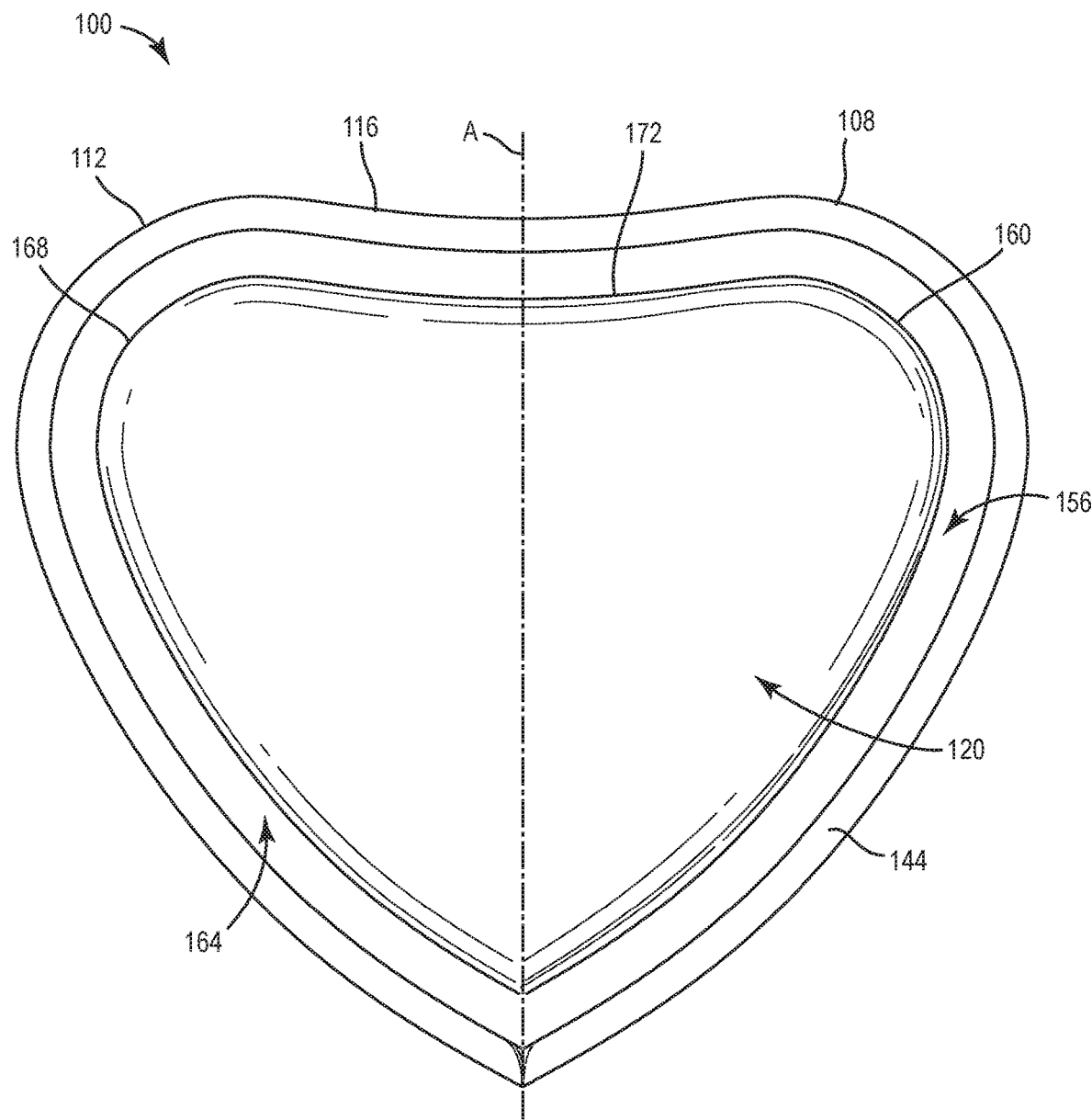
FIG. 1 is a front view of a wound dressing according to an exemplary embodiment.

Referring generally to the FIGURES, a wound therapy system for treating wounds of curved body parts is shown, according to various embodiments. More specifically, the wound therapy system is for treating wounds in the breast area, although the wound therapy system can also be deployed on other curved parts of the body, such as the buttocks, harvest sites for skin grafting (e.g. the back of a leg), and the lower back. The wound therapy system includes a wound dressing and a negative pressure wound therapy (NPWT) system. The phrase "negative pressure" means a pressure less than an ambient or atmospheric pressure. While the amount and nature of reduced pressure applied to the wound site can vary according to the application, the reduced pressure typically is between −5 mm Hg and −500 mm Hg and more typically between −100 mm Hg and −300 mm Hg. The wound dressing described herein is shaped to cover the entire breast area (e.g. extend between a side of the patient's rib cage generally beneath the armpit near the lymph node gland to the sternum region and an upper portion of the chest area). In some embodiments, the profile of the wound dressing is generally heart-shaped and includes a curved, slightly concave portion positionable proximate a patient's armpit, a first lobe (e.g. slightly convex) for covering an upper portion of the breast and a second lobe (e.g. slightly convex) for covering a bottom portion of the breast, curving around the ribcage, and extending beneath the armpit. In some embodiments, the profile of the wound dressing is generally shaped like a guitar pick (e.g., generally triangular and having curved sides and corners). The wound dressing described herein can be configured to conform to applications involving two-dimensional and/or three-dimensional contours. For example, when the wound dressing is used to treat a full and/or partial mastectomy, the dressing is configured to conform to a side of the patient's ribcage and a generally flat (e.g. two-dimensional) front portion of the patient's rib cage. In instances where the wound dressing is used to treat a partial mastectomy, a breast enhancement incision, or a breast reduction incision, the wound dressing is configured to conform to a side of the patient's ribcage and a curved (e.g. a three-dimensional) contour formed defined by the breast and the front portion of the ribcage. The profile shape of the wound dressing is generally symmetric to allow placement of the wound dressing on either the left or the right breast.

In the illustrated embodiments, the manifold layer of the wound dressing includes a scoring pattern to allow the manifold layer to bend to conform to three-dimensional curved shapes. The scores extend generally to a partial depth of the thickness (e.g. 7 mm, etc.) into the manifold layer. In some embodiments, the scoring pattern is generally hexagonal. In other embodiments, the scoring pattern is generally quadrilateral. For example, the scores may form squares, parallelograms, or rectangles. In other embodiments, the scoring pattern is concentric scoring following a shape of a perimeter of the manifold layer. The manifold layer is configured to wick fluid (e.g. exudate) from the wound and includes in-molded manifold layer structures for distributing negative pressure throughout the wound dressing during negative pressure wound therapy treatments.

In some embodiments, a portion of the scores in a central area of the manifold layer of the wound include perforations that extend through a width of the manifold layer. The perforations permit selective removal of one or more pieces of the manifold layer to allow visualization of the nipple when the wound dressing is secured to a patient. Visualization of the nipple is intended to allow a healthcare practitioner to observe the health of the wound while leaving the dressing intact.

The wound therapy system may include a removed-fluid container and a pump. The removed-fluid container can be configured to store a fluid removed from the wound site (e.g., wound exudate, etc.). The removed-fluid container can be fluidly coupled to the wound site via a fluid removal line. The NPWT can help reduce the chance of the wounds developing seroma, scaring, infection, or other adverse complications.

In some embodiments, when two wound dressings are used on the same patient, the two wound dressings can be connected using a Y-connection so that the same pump and removed-fluid container can be used to treat the wounds. The pump and/or the Y-connection can include at least one valve so that different amounts of negative pressure can be exerted on each breast if desired.

Additional features and advantages of the wound therapy system are described in detail below.

Wound Dressing

Figure 2:
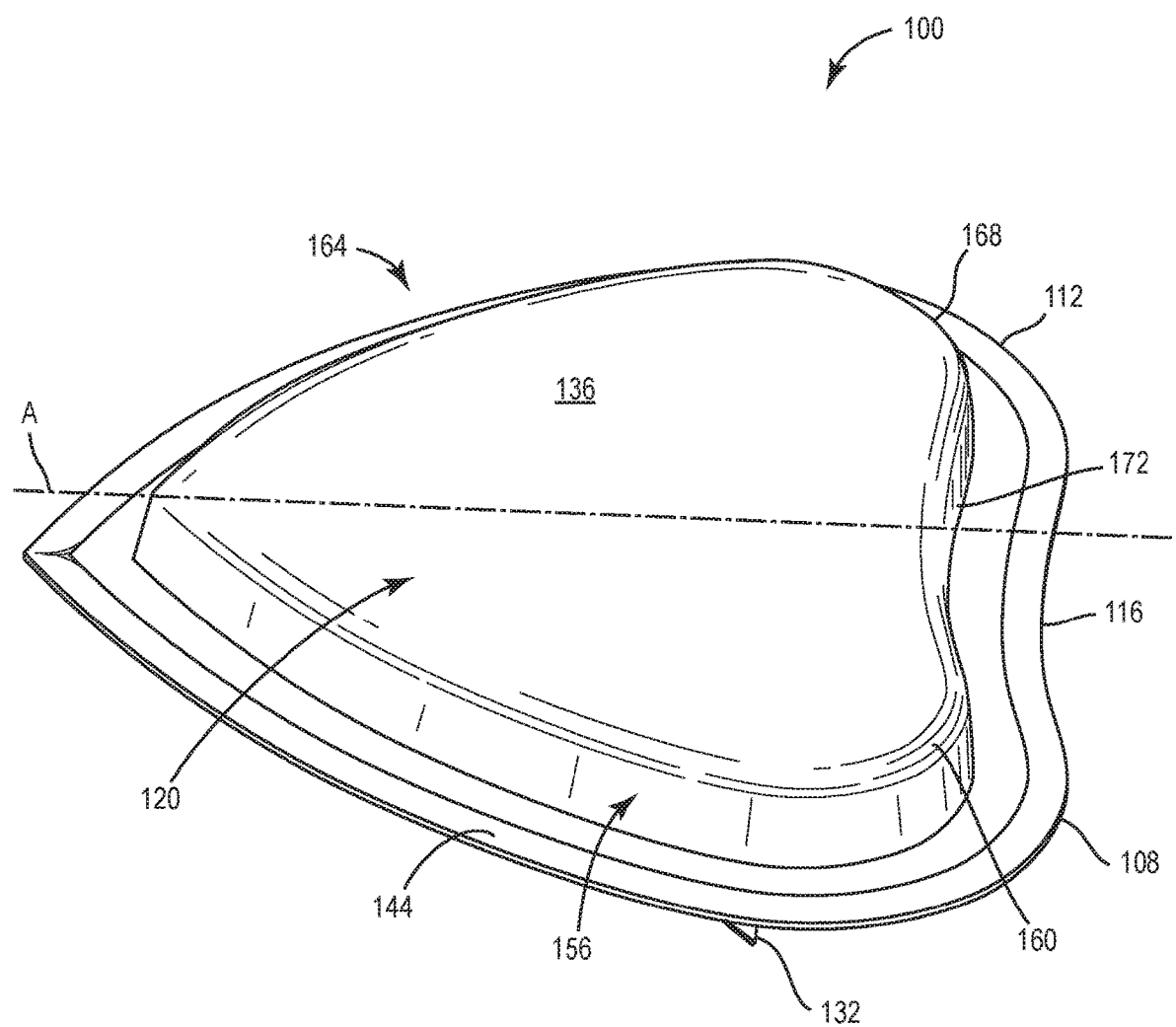
FIG. 2 is a perspective view of the wound dressing of FIG. 1 according to an exemplary embodiment.
Figure 3:
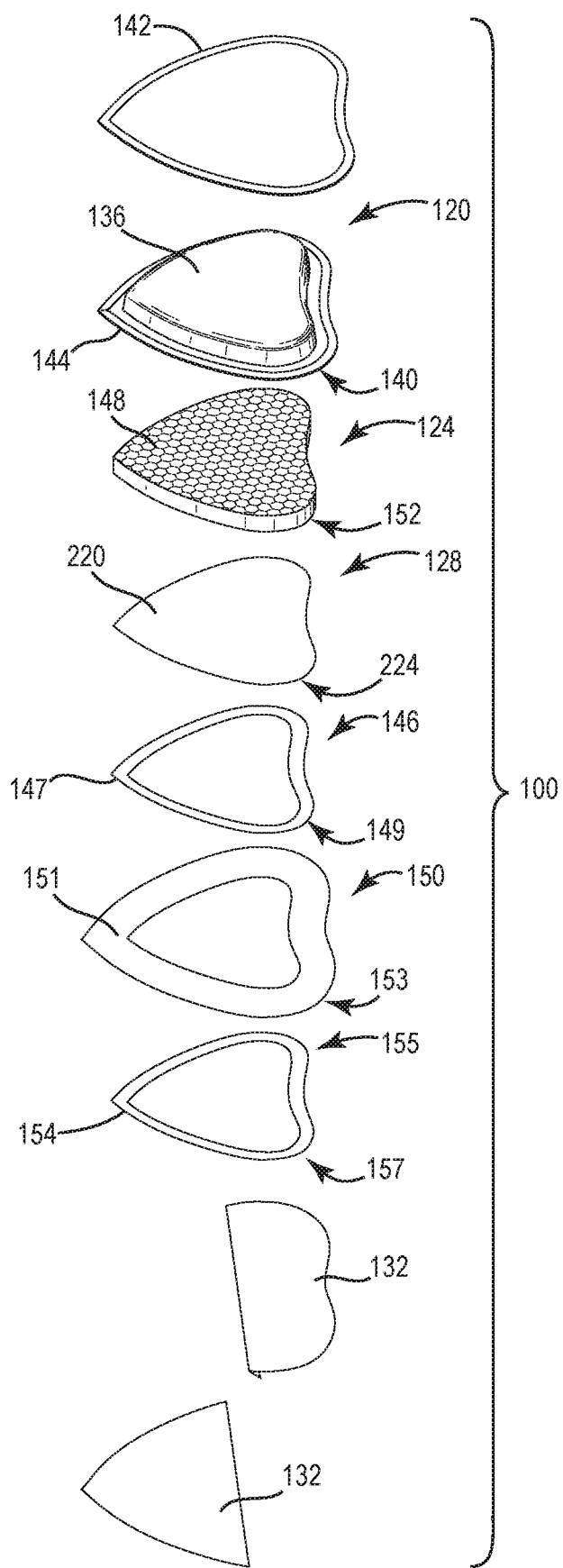
FIG. 3 is an exploded view of the wound dressing of FIG. 1 according to an exemplary embodiment.
Figure 4:
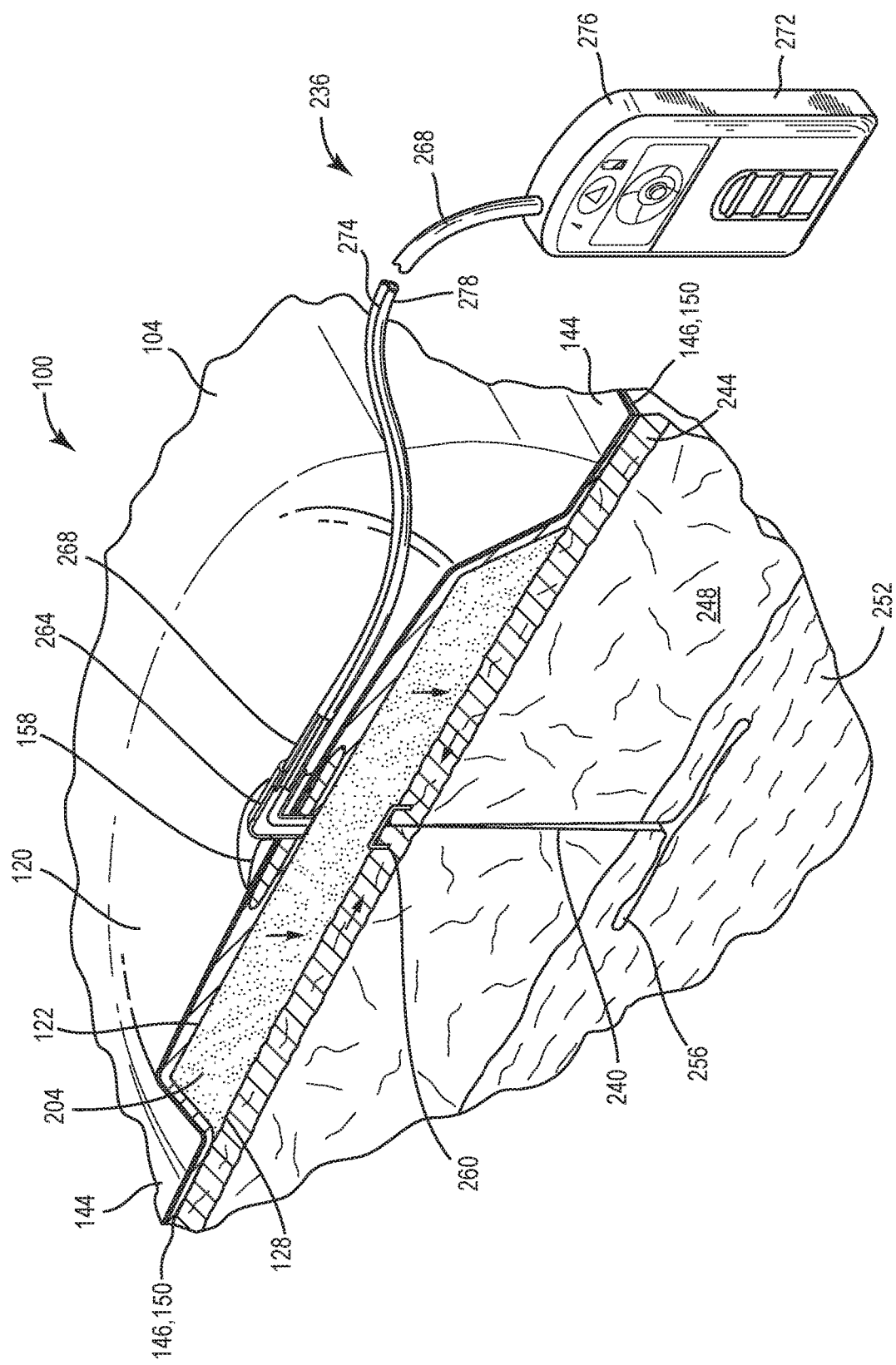
FIG. 4 is a side cross-sectional view of the wound dressing of FIG. 1 adhered to a patient according to an exemplary embodiment.

Referring now to FIGS. 1-4, a wound dressing 100 is shown, according to an exemplary embodiment. FIG. 1 is a front view of the wound dressing 100. FIG. 2 is a perspective view of the wound dressing 100. FIG. 3 is an exploded view illustrating several layers 120-154 of the wound dressing 100. FIG. 4 is a cross-sectional view of the wound dressing 100 adhered to a surface 104, such as a patient's torso.

In various embodiments, the wound dressing 100 can be formed as a substantially flat sheet for topical application to wounds. The wound dressing 100 can lie flat for treatment of substantially flat wounds and is also configured to bend to conform to body surfaces having high curvature, such as breasts. The wound dressing 100 has a profile or a perimeter that is generally heart-shaped and includes a first lobe 108 (e.g. convex portion) and a second lobe 112 (e.g. convex portion) that define a concave portion 116 therebetween. The wound dressing 100 is generally symmetric about an axis A. It is contemplated that the size of the wound dressing can range from 180 cm$^2$ to 1000 cm$^2$. More preferably, the size of the wound dressing can range from 370 cm$^2$ to 380 cm$^2$, 485 cm$^2$ to 495 cm$^2$, and/or 720 cm$^2$ to 740 cm$^2$. However, other shapes and sizes of wound dressing 100 are also possible depending on the intended use. For example, for some uses, the wound dressing 100 may have asymmetrically-shaped lobes 108, 112.

The wound dressing 100 is shown to include a plurality of layers, including a drape layer 120, a manifold layer 124, a wound-interface layer 128, a rigid support layer 142, a first adhesive layer 146, a second adhesive layer 150, and a patient-contacting layer 154. In some embodiments, the wound dressing 100 includes a removable cover sheet 132 to cover the manifold layer 124, the wound-interface layer 128, the second adhesive layer 150, and/or the patient-contacting layer 154 before use.

Drape Layer

The drape layer 120 is shown to include a first surface 136 and a second, wound-facing, surface 140 opposite the first surface 136. When the wound dressing 100 is applied to a wound, the first surface 136 faces away from the wound, whereas the second surface 140 faces toward the wound. The drape layer 120 supports the manifold layer 124 and the wound-interface layer 128 and provides a barrier to passage of microorganisms through the wound dressing 100. The drape layer 120 is configured to provide a sealed space over a wound or incision. In some embodiments, the drape layer 120 is an elastomeric material or may be any material that provides a fluid seal. "Fluid seal" means a seal adequate to hold pressure at a desired site given the particular reduced-pressure subsystem involved. The term "elastomeric" means having the properties of an elastomer and generally refers to a polymeric material that has rubber-like properties. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. As non-limiting examples, the drape layer 120 may be formed from materials that include a silicone, 3M Tegaderm® drape material, acrylic drape material such as one available from Avery, or an incise drape material.

The drape layer 120 may be substantially impermeable to liquid and substantially permeable to water vapor. In other words, the drape layer 120 may be permeable to water vapor, but not permeable to liquid water or wound exudate. This increases the total fluid handling capacity (TFHC) of wound dressing 100 while promoting a moist wound environment. In some embodiments, the drape layer 120 is also impermeable to bacteria and other microorganisms. In some embodiments, the drape layer 120 is configured to wick moisture from the manifold layer 124 and distribute the moisture across the first surface 136.

Figure 9:
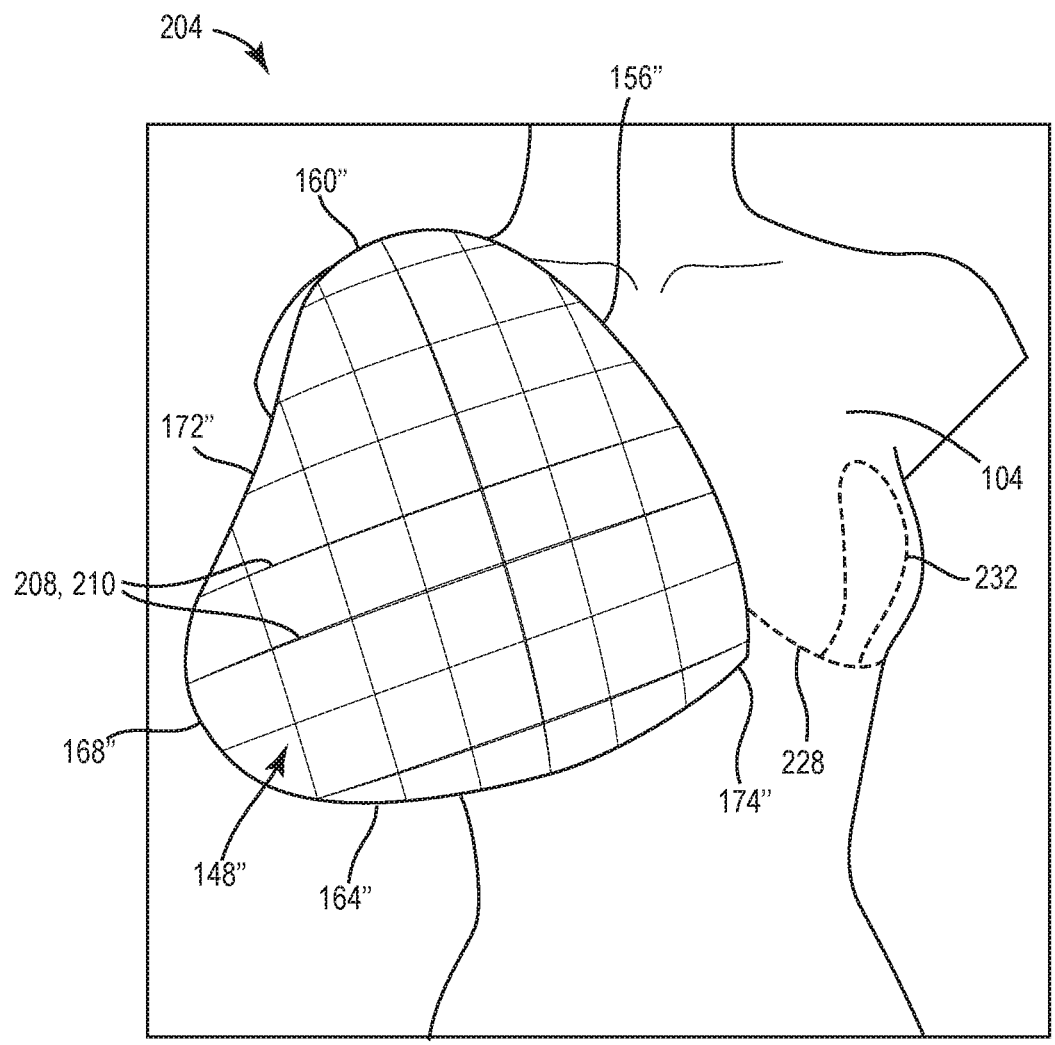
FIG. 9 is a top view of the wound dressing of FIG. 1 aligned with a representative person's torso.
Figure 10:
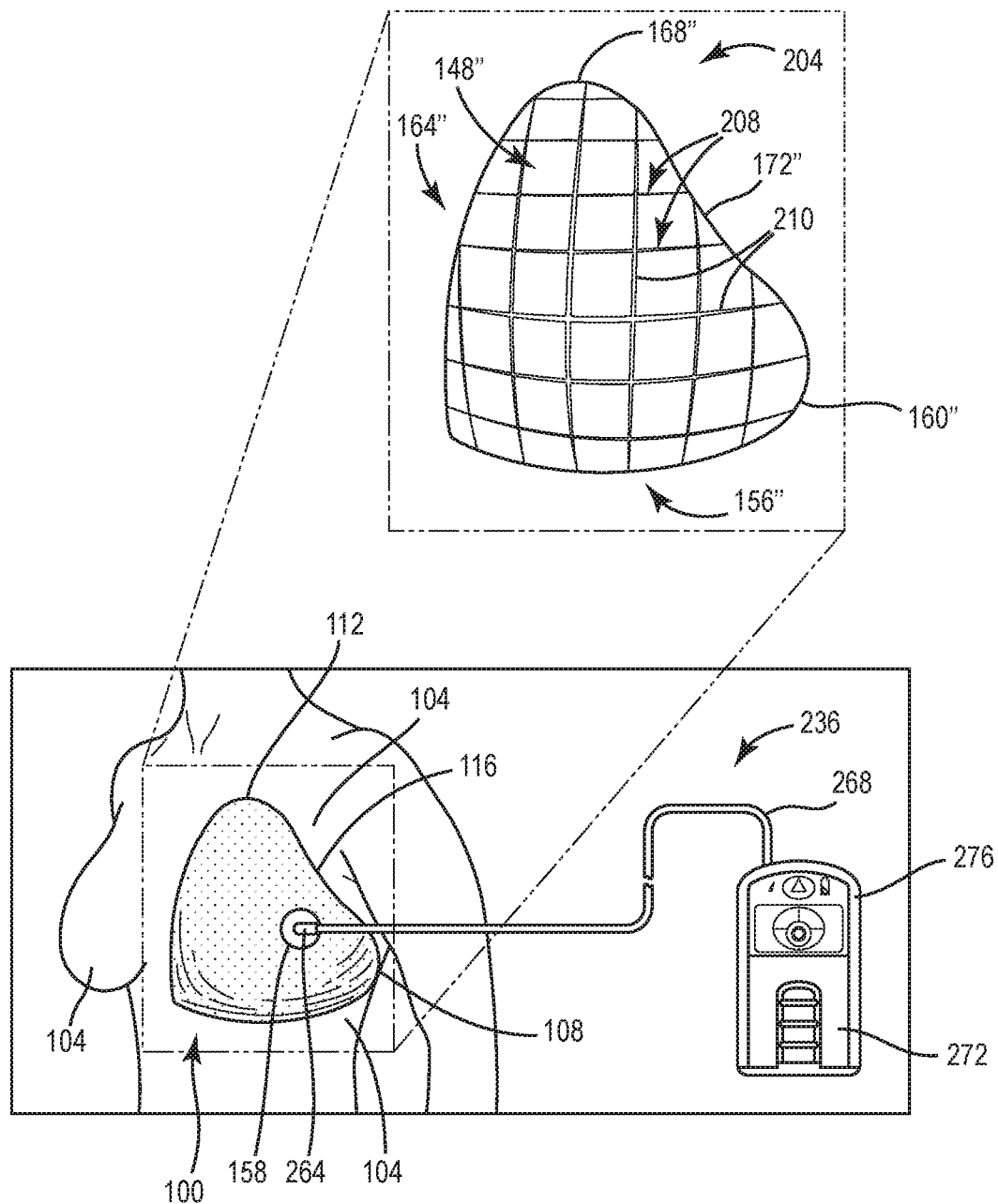
FIG. 10 is a perspective view of the wound dressing of FIG. 1 adhered to a representative person's torso.

In the illustrated embodiment, the drape layer 120 defines a cavity 122 (FIG. 4) for receiving the manifold layer 124, the wound-interface layer 128, and the first adhesive layer 146. As shown in FIG. 2, the manifold layer 124, the wound-interface layer 128, and the first adhesive layer 146 can have a similar perimeter or profile. In some embodiments, a perimeter of the drape layer 120 extends beyond (e.g. circumscribes) the perimeter of the manifold layer 124 to provide a margin 144. The first adhesive layer 146 includes a first surface 147 and a second, wound-facing surface 149. Both first surface 147 and the second surface 149 are coated with an adhesive, such as an acrylic adhesive, a silicone adhesive, and/or other adhesives. The first surface 147 of the first adhesive layer 146 is secured to the second surface 224 of the wound-interface layer 128. The second surface 149 of the first adhesive layer 146 is secured to the second adhesive layer 150. The second adhesive layer 150 includes a first surface 151 and a second, wound-facing surface 153. The second surface 149 of the first adhesive layer 146 is secured to the first surface 151 of the second adhesive layer 150. The second surface 153 of the second adhesive layer 150 is coated with an acrylic adhesive, a silicone adhesive, and/or other adhesives. The adhesive applied to the second surface 153 of the second adhesive layer 150 is intended to ensure that the wound dressing 100 adheres to the surface 104 of the patient's skin (as shown in FIGS. 4, 9, and 10) and that the wound dressing 100 remains in place throughout the wear time. The second adhesive layer 150 has a perimeter or profile that is similar to a perimeter or profile of the margin 144. In the illustrated embodiment, the first surface 151 of the second adhesive layer 150 is welded to the margin 144. In other embodiments, the first surface 151 of the second adhesive layer is secured to the margin 144 using an adhesive, such as an acrylic adhesive, a silicone adhesive, or another type of adhesive. The patient-contacting layer 154 includes a first surface 155 and a second, wound-facing surface 157. In some embodiments, the patient-contacting layer 154 can be made of a hydrocolloid material, a silicone material or another similar material. The first surface 155 of the patient-contacting layer 154 can be secured to the second adhesive layer 150. The patient-contacting layer 154 follows a perimeter of the manifold layer 124. In some embodiments, the patient-contacting layer 154 can be made of a polyurethane film coated with an acrylic or silicone adhesive on both surfaces 155, 157. In some embodiments, the patient-contacting layer 154 can include a hydrocolloid adhesive on the second, wound-facing, surface 157. The margin 144 and/or the second adhesive layer 150 may extend around all sides of the manifold layer 124 such that the wound dressing 100 is a so-called island dressing. In other embodiments, the margin 144 and/or the second adhesive layer 150 can be eliminated and the wound dressing 100 can be adhered to the surface 104 using other techniques. In some embodiments, the first adhesive layer 146, the second adhesive layer 150, and the patient-contacting layer 154 can collectively form a base layer that includes an adhesive on both sides that is (i) configured to secure the drape layer 120 to the manifold layer 124, the optional wound-interface layer 128, and (ii) configured to secure the wound dressing 100 to a patient's tissue. In some embodiments, the base layer can be integrally formed with the drape layer 120. In some embodiments, the base layer can be a layer of a polyurethane film having a first surface and a second, wound-facing surface. Both the first surface and the second surface can be coated with an adhesive (such as an acrylic or silicone adhesive). In some embodiments, the wound-facing surface of the base layer can include a hydrocolloid adhesive.

In some embodiments, a reduced-pressure interface 158 can be integrated with the drape layer 120. The reduced-pressure interface 158 can be in fluid communication with the negative pressure system through a removed fluid conduit 268 (FIG. 4). The reduced-pressure interface 158 is configured to allow fluid communication between a negative pressure source and the wound dressing 100 (e.g., through the drape layer 120) via a removed fluid conduit coupled between the reduced-pressure interface 158 and the negative pressure source such that negative pressure generated by the negative pressure source can be applied to the wound dressing 100 (e.g., through the drape layer 120). In some embodiments, the reduced-pressure interface 158 can be integrated (e.g., integrally formed) with the drape layer 120. In other embodiments, the reduced-pressure interface 158 can be separate from the drape layer 120 and configured to be coupled to the drape layer 120 by a user.

With continued reference to FIG. 2, the rigid support layer 142 is positioned above the first surface 136 of the drape layer 120. The rigid support layer 142 is spaced from but proximate the margin 144 and the second adhesive layer 150. The rigid support layer 142 is made of a rigid material and helps the wound dressing 100 maintain rigidity before the wound dressing 100 is secured to the surface 104 of the patient. The rigid support layer 142 is intended to be removed from the drape layer 120 after the wound dressing 100 has been secured to the surface 104 of the patient.

In some embodiments, the second surface 140 of the drape layer 120 contacts the manifold layer 124. The second surface 140 of the drape layer 120 may be adhered to the manifold layer 124 or may simply contact the manifold layer 124 without the use of an adhesive.

In some embodiments, the adhesive applied to the second surface 140 of the drape layer 120 is moisture vapor transmitting and/or patterned to allow passage of water vapor therethrough. The adhesive may include a continuous moisture vapor transmitting, pressure-sensitive adhesive layer of the type conventionally used for island-type wound dressings (e.g. a polyurethane-based pressure sensitive adhesive).

Manifold Layer

Figure 5:
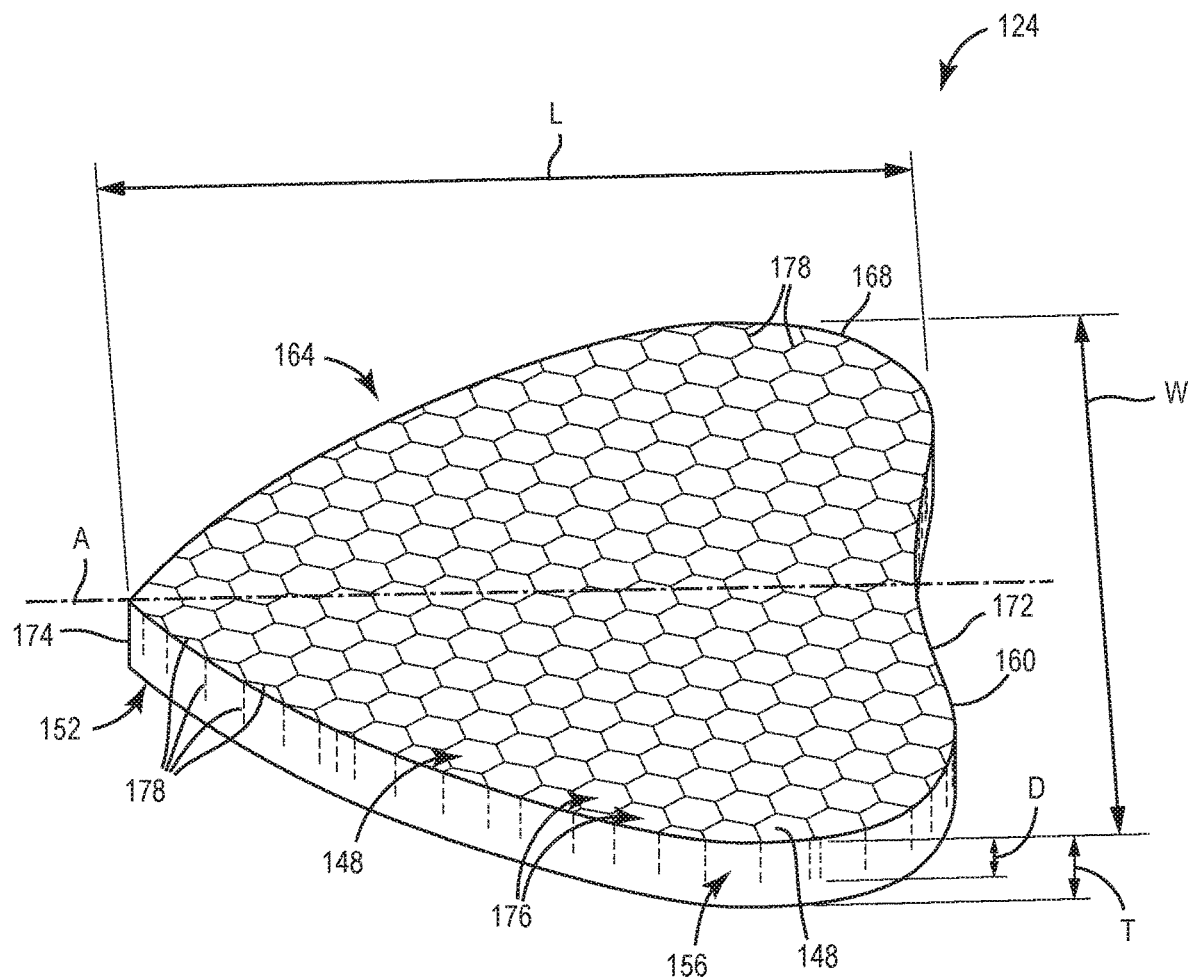
FIG. 5 is a perspective view of a manifold layer of the wound dressing of FIG. 1 according to an exemplary embodiment.

Referring to FIG. 5, the manifold layer 124 is shown to include a first surface 148 and a second, wound-facing surface 152 opposite the first surface 148. When the wound dressing 100 is applied to a wound, the first surface 148 faces away from the wound, whereas the second surface 152 faces toward the wound. In some embodiments, the first surface 148 of the manifold layer 124 contacts the second surface 140 of the drape layer 120. In some embodiments, the second surface 152 of the manifold layer 124 contacts the wound-interface layer 128. The manifold layer 124 is configured for transmission of negative pressure to the patient's tissue at and/or proximate a wound and/or incision. The manifold layer 124 is configured to wick fluid (e.g. exudate) from the wound and includes in-molded manifold layer structures for distributing negative pressure throughout the wound dressing 100 during negative pressure wound therapy treatments.

The manifold layer 124 can be made from a porous and permeable foam-like material and, more particularly, a reticulated, open-cell polyurethane or polyether foam that allows good permeability of wound fluids while under a reduced pressure. One such foam material that has been used is the V.A.C.® Granufoam™ material that is available from Kinetic Concepts, Inc. (KCI) of San Antonio, Tex. Any material or combination of materials might be used for the manifold layer 124 provided that the manifold layer 124 is operable to distribute the reduced pressure and provide a distributed compressive force along the wound site.

The reticulated pores of the Granufoam™ material that are in the range from about 400 to 600 microns, are preferred, but other materials may be used. The density of the manifold layer material, e.g., Granufoam™ material, is typically in the range of about 1.3 lb/ft$^3$-1.6 lb/ft$^3$ (20.8 kg/m$^3$-25.6 kg/m$^3$). A material with a higher density (smaller pore size) than Granufoam™ material may be desirable in some situations. For example, the Granufoam™ material or similar material with a density greater than 1.6 lb/ft$^3$ (25.6 kg/m$^3$) may be used. As another example, the Granufoam™ material or similar material with a density greater than 2.0 lb/ft$^3$ (32 kg/m$^3$) or 5.0 lb/ft$^3$ (80.1 kg/m$^3$) or even more may be used. The more dense the material is, the higher compressive force that may be generated for a given reduced pressure. If a foam with a density less than the tissue at the tissue site is used as the manifold layer material, a lifting force may be developed. In one illustrative embodiment, a portion, e.g., the edges, of the wound dressing 100 may exert a compressive force while another portion, e.g., a central portion, may provide a lifting force.

The manifold layer material may be a reticulated foam that is later felted to thickness of about one third (⅓) of the foam's original thickness. Among the many possible manifold layer materials, the following may be used: Granufoam™ material or a Foamex® technical foam (www-.foamex.com). In some instances it may be desirable to add ionic silver to the foam in a microbonding process or to add other substances to the manifold layer material such as antimicrobial agents. The manifold layer material may be isotropic or anisotropic depending on the exact orientation of the compressive forces that are desired during the application of reduced pressure. The manifold layer material may also be a bio-absorbable material.

As shown in FIGS. 1-3 and 5, the manifold layer 124 is generally symmetrical, heart-shaped, and includes a first convex curved side 156 defining a first lobe 160, a second convex curved side 164 defining a second lobe 168, and a concave connecting portion 172 extending therebetween. The manifold layer 124 can have a width W ranging between 8 cm and 33 cm, and more preferably between 17 cm and 33 cm. The manifold layer 124 can have a length L ranging between 7 cm and 35 cm, and more preferably between 14 cm and 30 cm. The manifold layer 124 can have a thickness T ranging between 14 mm and 24 mm, and more preferably 19 mm. The first lobe 160 and the second lobe 168 are convex and can have a radius of curvature ranging between 3 cm and 10 cm, and more preferably from 5 cm to 9 cm. The connecting portion 172 is generally concave and can have a radius of curvature ranging between 20 cm and 33 cm, and more preferably from 22 cm to 28 cm. The first curved side 156 and the second curved side 164 form a point 174 positioned generally opposite the connecting portion 172. In the illustrated embodiment, the first curved side 156 and the second curved side 164 are generally symmetric about the axis A.

As is best shown in FIG. 5, a scoring pattern 176 is formed in the first surface 148 of the manifold layer 124. The scoring pattern 176 is shown for example as an arrangement of "slits" or scores (e.g., "mango-cuts") formed in the manifold layer 124 (e.g. formed by laser-scoring or other suitable processes). More particularly, the scoring pattern 176 is cut into the first surface 148 of the manifold layer 124. In the embodiment of FIG. 5, the scoring pattern 176 extends between the first surface 148 and the second surface 152 but does not extend completely to the second surface 152. The scoring pattern 176 can have a depth D that ranges between 5 mm and 12 mm, and more preferably is approximately 7 mm. According to the illustrated embodiment, the scoring pattern 176 is a generally hexagonal pattern. However, in other embodiments, the scoring pattern 176 can be a different geometrical pattern. When the wound dressing 100 is used on a generally flat (e.g. two-dimensional) surface 104 or portion of a surface 104, such as for example a front of a patient's ribcage after a mastectomy or a side of the patient's ribcage, the scores 178 of the scoring pattern 176 are generally vertical and are in close proximity to adjacent scores 178 of the scoring pattern 176. In instances when the wound dressing 100 is secured to a curved (e.g. three-dimensional) surface, such as a breast or a transition portion of the surface that extends between the side of the ribcage and the front of the ribcage, the scores 178 of the scoring pattern 176 splay apart to facilitate bending of the manifold layer 124 so that the manifold layer 124 closely conforms to the shape of the curved surface 104. The scoring pattern 176 allows the manifold layer 124 to conform to both substantially flat surfaces and to a wide range of curved surfaces 104. The hexagonal scoring pattern 176 facilitates conforming to highly curved surfaces 104 by providing six scores 178 about which the manifold layer 124 can bend (e.g. the manifold layer 124 can bend in six different directions proximate each hexagon cut into the first surface 148). In implementations where the surface 104 is the breast or is proximate the breast of a patient, the scoring pattern 176 allows a single size of manifold layer 124 to conform to varying sizes of breasts.

Figure 6:
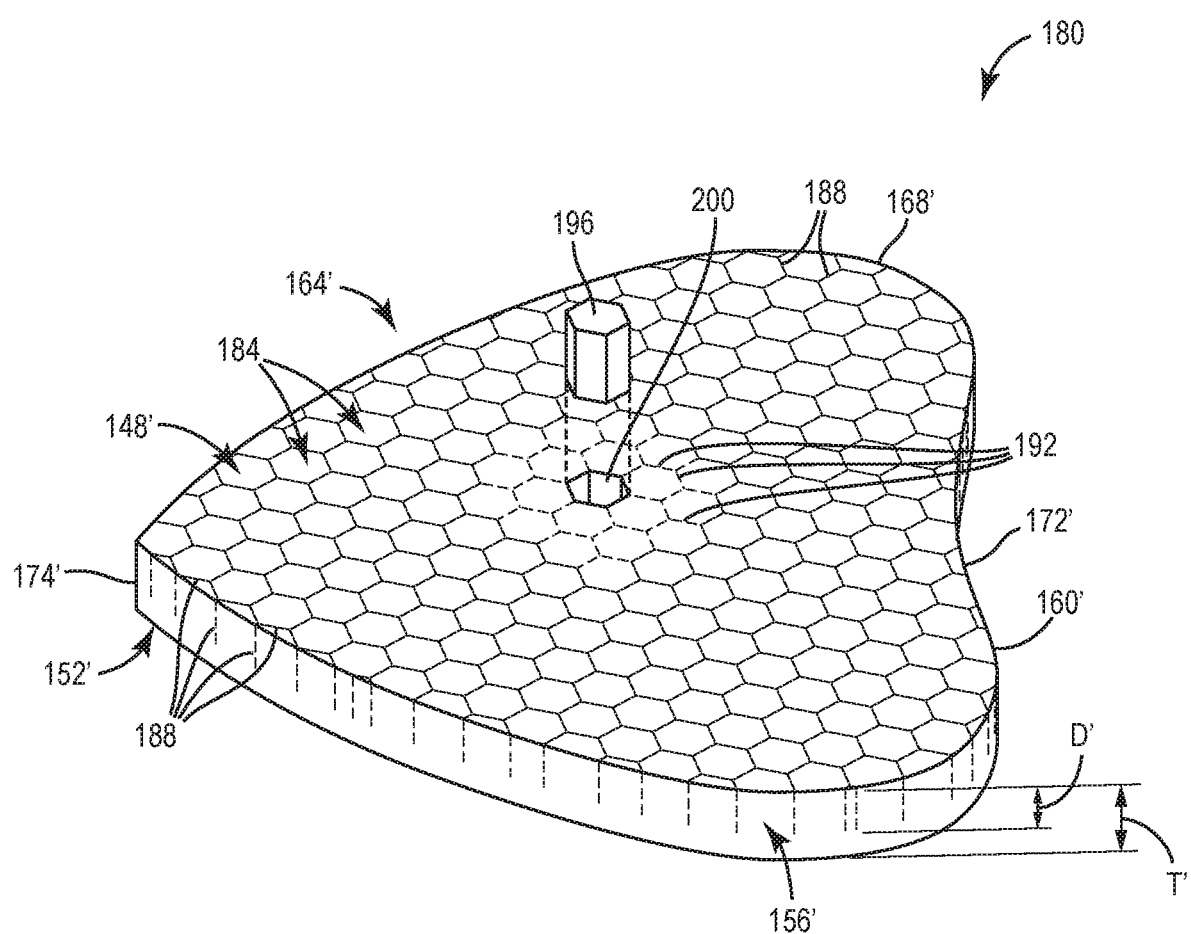
FIG. 6 is an exploded view of a manifold layer of the wound dressing of FIG. 1 according to another exemplary embodiment.

FIG. 6 illustrates a manifold layer 180 according to another embodiment. The manifold layer 180 is generally similar to the manifold layer 124. The manifold layer 180 can be incorporated into the wound dressing 100 as described above with respect to the manifold layer 124. Like numbers are indicated by the same number and parts of the manifold layer 180 are indicated using the prime symbol "'".

The manifold layer 180 includes a scoring pattern 184 formed in the first surface 148'. The scoring pattern 184 is shown for example as an arrangement of "slits" or scores (e.g., "mango-cuts") formed in the manifold layer 180 (e.g. formed by laser-scoring or other suitable processes). Preferably, the scoring pattern 184 is cut into the first surface 148'. In the embodiment shown in FIG. 6, the scoring pattern 184 is a hexagonal pattern. In other embodiments, the scoring pattern 184 can be a different geometrical pattern. The scoring pattern 184 includes a first portion 188 of scores proximate a perimeter of the manifold layer 180 and a second portion 192 of scores proximate a center of the manifold layer 180. The first portion 188 of scores, which are shown in phantom in FIG. 6, extends from the first surface 148' toward the second surface 152', but does not penetrate the second surface 152'. The first portion 188 of scores can have a depth D' that ranges between 5 mm and 12 mm, and more preferably is approximately 7 mm. The second portion 192 of scores, which is indicated by the dashed lines in FIG. 6, include a cut portion and a perforated portion. The perforations of the perforated portion penetrate through to the second surface 152'. The perforations facilitate removal of at least one piece 196 of the second portion 192 of the manifold layer 124. FIG. 6 illustrates a piece 196 of the manifold layer 180 that has been removed to form a through-opening 200 in the manifold layer 180. The through-opening 200 allows for visualization of the wound through the manifold layer 180 when the wound dressing 100 is secured to the patient. More particularly, when the manifold layer 180 is used to treat wounds in the breast area, the second portion 192 is positioned to cover a center of the breast so that at least one piece 196 of the second portion 192 can be selectively removed to allow visualization of the nipple. Visual inspection of the color of the nipple is generally understood to be indicative of the health and/or condition of the wounds in the breast area while the dressing remains intact and without interrupting the negative pressure therapy of the wound. To facilitate viewing of the wound through the wound dressing 100, the drape layer 120 is preferably transparent in embodiments of the wound dressing 100 that include the manifold layer 180.

Figure 7:
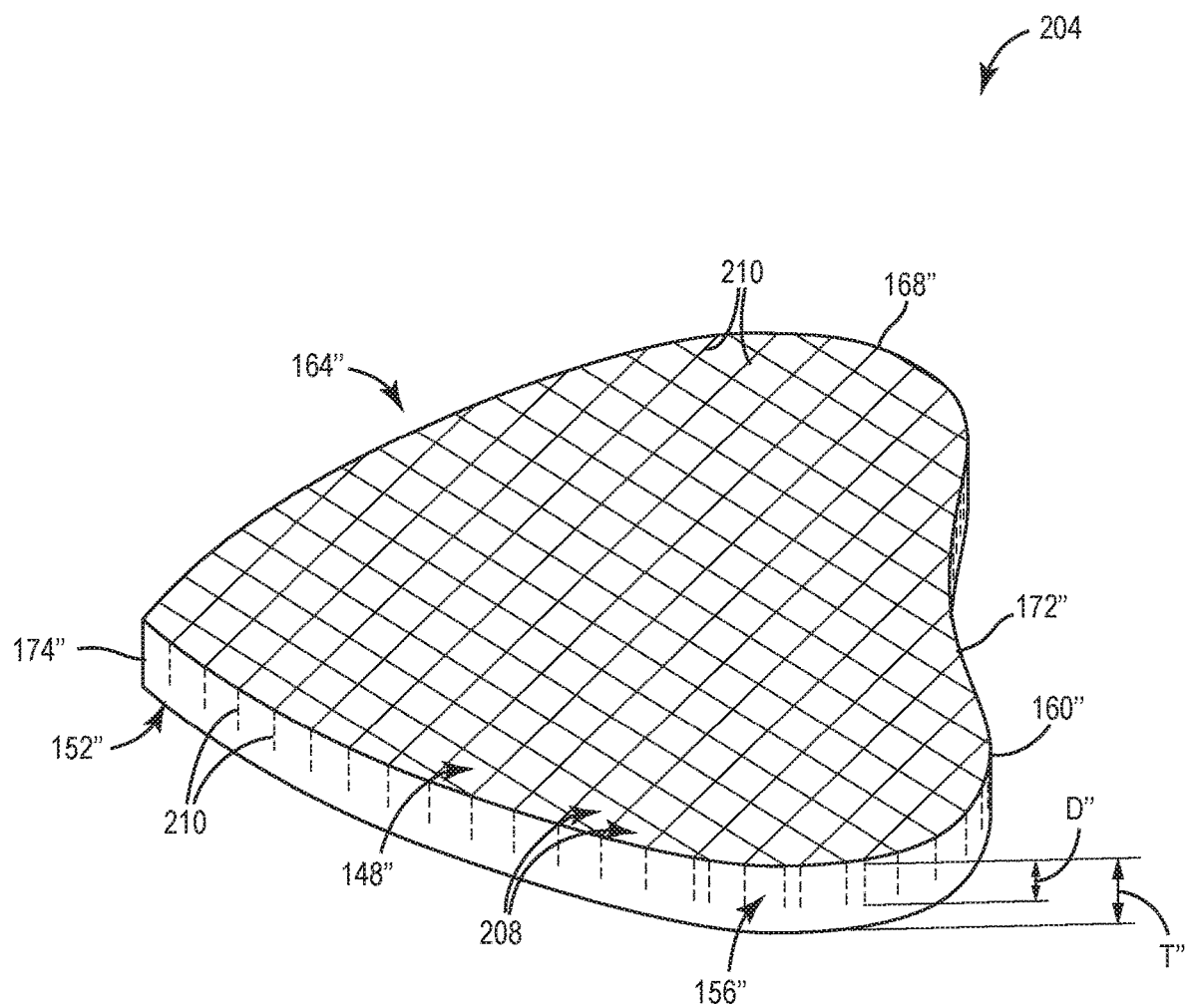
FIG. 7 is a perspective view of a manifold layer of the wound dressing of FIG. 1 according to another exemplary embodiment.

FIG. 7 illustrates a manifold layer 204 according to another embodiment. The manifold layer 204 is generally similar to the manifold layer 124. The manifold layer 204 can be incorporated into the wound dressing 100 as described above with respect to the manifold layer 124. Like numbers are indicated by the same number and parts of the manifold layer 204 are indicated using the double prime symbol "''".

The manifold layer 204 includes a scoring pattern 208 formed in the first surface 148". The scoring pattern 208 is shown for example as an arrangement of "slits" or scores (e.g., "mango-cuts") formed in the manifold layer 204 (e.g. formed by laser-scoring or other suitable processes). More particularly, the scoring pattern 208 is cut into the first surface 148". In the embodiment shown in FIG. 7, the scoring pattern 208 is a generally square pattern. In other embodiments, the scoring pattern 208 can be a different geometrical shape, for example, rectangular, parallelogram, diamond, rhombus, or any other quadrilateral shape. In the embodiment of FIG. 7, the scoring pattern 208 extends between the first surface 148" and the second surface 152" but does not extend completely through to the second surface 152". The scoring pattern 208 can have a depth D" that ranges between 5 mm and 12 mm, and more preferably is 7 mm. In other embodiments, the scoring pattern 208 can facilitate removal of at least some of a center portion of the manifold layer 204 as described above with respect to FIG. 6. When the wound dressing 100 is used on a generally flat (e.g. two-dimensional) surface 104 or portion of a surface 104, such as for example a front of a patient's ribcage after a mastectomy or a side of the patient's ribcage, the scores 210 of the scoring pattern 208 are generally vertical and are in close proximity to adjacent scores 210. In instances when the wound dressing 100 is secured to a curved (e.g. three-dimensional) surface 104, such as a breast or a transition portion of the surface 104 that extends between the side of the ribcage and the front of the ribcage, the scores 210 of the scoring pattern 208 splay apart to facilitate bending of the manifold layer 204 so that the manifold layer 204 closely conforms to the shape of the curved surface 104. The scoring pattern 208 allows the manifold layer 204 to conform to both substantially flat surfaces and to a wide range of curved surfaces 104. The square scoring pattern 208 facilitates conforming to curved surfaces 104 by providing four scores 210 about which the manifold layer 204 can bend (e.g. the manifold layer can bend in four different directions proximate each square cut into the first surface 148"). In implementations where the surface 104 is the breast or is proximate the breast of a patient, the scoring pattern 208 allows a piece of manifold layer 204 to conform to varying sizes of breasts.

Figure 8:
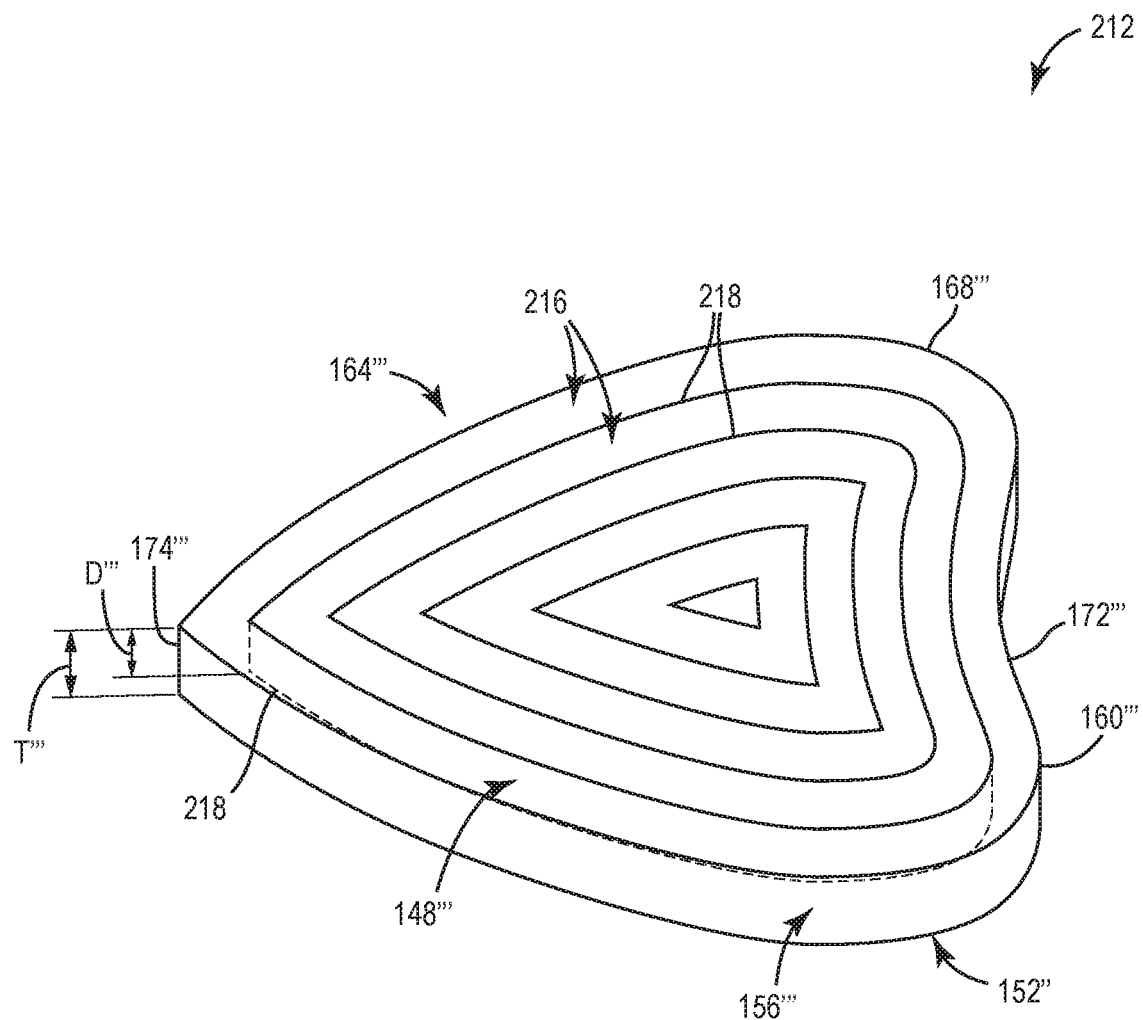
FIG. 8 is a perspective view of a manifold layer of the wound according to another exemplary embodiment.

FIG. 8 illustrates a manifold layer 212 according to a different embodiment. The manifold layer 212 is generally similar to the manifold layer 124. The manifold layer 212 can be incorporated into the wound dressing 100 as described above with respect to the manifold layer 124. Like numbers are indicated by the same number and parts of the manifold layer 212 are indicated using the triple prime symbol "'''".

The manifold layer 212 includes a scoring pattern 216 formed in the first surface 148'''. The scoring pattern is shown for example as an arrangement of "slits" or scores formed in the manifold layer 212 (e.g. formed by laser-scoring or other suitable processes). Preferably, the scoring pattern 216 is cut into the first surface 148'''. In the embodiment shown in FIG. 8, the scoring pattern 216 includes concentric scores 218 in a shape of a perimeter of the manifold layer 212. In the embodiment of FIG. 8, the scoring pattern 216 extends between the first surface 148' and the second surface 152''' but does not extend completely through to the second surface 152'. The scoring pattern 216 can have a depth D''' that ranges between 5 mm and 12 mm, and more preferably is approximately 7 mm. In instances where the wound dressing 100 is used on a generally flat (e.g. two-dimensional) surface 104 or portion of a surface 104, such as for example a front of a patient's ribcage after a mastectomy or a side of the patient's ribcage, the scores of the scoring pattern 216 are generally vertical and are in close proximity to adjacent scores. In instances when the wound dressing 100 is secured to a curved (e.g. three-dimensional) surface 104, such as a breast or a transition portion of the surface 104 that extends between the side of the ribcage and the front of the ribcage, the scores 218 of the scoring pattern 216 splay apart to facilitate bending of the manifold layer 212 so that the manifold layer 212 closely conform to the shape of the curved surface 104. The scoring pattern 216 allows the manifold layer 212 to conform to both substantially flat surfaces and a wide range of curved surfaces 104. In implementations where the surface 104 is or is proximate the breast area of a patient, the scoring pattern 216 allows a single size of manifold layer 212 to conform to varying sizes of breasts.

Some embodiments may include manifold layers having a first geometric pattern and a second geometric pattern different than the first geometric pattern. In such embodiments, the first geometric pattern may have more sides than the second geometric pattern, and thus be able to conform to a more highly curved shape. In such an embodiment, the first geometric pattern may be positioned proximate a center of the manifold layer and the second geometric pattern may be positioned proximate a perimeter of the manifold layer.

Wound-Interface Layer

The wound-interface layer 128 is shown to include a first surface 220 and a second, wound-facing surface 224 opposite the first surface 220. When the wound dressing 100 is applied to the wound, the first surface 220 faces away from the wound, whereas the second surface 152 faces toward the wound. In some embodiments, the first surface 220 of the wound-interface layer 128 contacts the second surface 224 of the manifold layer 124. In some embodiments, the second surface 224 of the wound-interface layer 128 contacts the surface 104 of the patient. In some embodiments, the wound dressing 100 may not include the wound-interface layer 128.

The wound-interface layer 128 is made of a wicking material that is fluid-permeable and intended to not irritate the patient's skin. In the illustrated embodiment, the wound-interface layer is a polyester pique-knit fabric, such as Milliken Fabric. In other embodiments, other permeable and non-irritating fabrics can be used. The wound-interface layer 128 can also be treated with antimicrobial materials. In the illustrated embodiment, the wound-interface layer 128 includes silver ions as an antimicrobial material. Other anti-microbial materials may be used in other embodiments.

Deployment of the Dressing

FIG. 9 illustrates the manifold layer 204 positioned proximate a representative model of a woman's torso. While the manifold layer 204 is shown in FIGS. 9 and 10, the manifold layers 124, 180, and 212 can be deployed in a similar manner. Exemplary intersecting incisions used in breast surgeries such as full and/or partial mastectomies, breast enhancements, and/or breast reductions are shown on a left breast of the model. Although FIG. 9 illustrates the manifold layer 204, the wound dressing 100 is positioned on the patient in a similar manner. A first incision 228 is positioned proximate the bottom (e.g. towards the feet) of the breast. A second incision 232 extends upward (e.g. towards the head) from the first incision 228, surrounds the nipple, and extends downward toward the first incision 228. Such intersecting incisions are typically referred to as T-shaped incisions. Breast surgeries may include further incisions proximate the armpit and/or the lymph node proximate the armpit (not shown). As shown in FIG. 9, the manifold layer 204 (and the wound dressing 100) is sized to cover the surface including the entire breast area, including the first incision 228, the second incision 232, and any incisions proximate the armpit. A further advantage of covering the entire breast area is that the manifold layer 204 (and the wound dressing 100) can provide support to the whole breast area during the negative pressure therapy. In some embodiments, the wound dressing 100 can be used with topically applied pharmaceutical compounds. For example, the wound dressing 100 can be used in conjunction with a silicone gel applied proximate the first incision 228 and the second incision 232. The silicone gel can reduce scarring at or near the incisions 228, 232. In another example, the wound dressing 100 can be used in conjunction with a nitroglycerin ointment applied at or near the nipple area. The nitroglycerin ointment can increase perfusion at or near the nipple area.

FIG. 9 illustrates by way of example the manifold layer 204 positioned above a surface 104 defined by the right breast for treatment of the right breast area. When the manifold layer 204 is used to support the right breast, the manifold layer 204 is positioned so that the connecting portion 172'' is positioned proximate the right armpit. The first lobe 160'' covers an upper portion of the breast area. The second lobe 168'' covers a bottom portion of the breast area and can be curved around the body to cover a portion of a right side of the torso. The point 174'' is positioned proximate a bottom of the sternum. By comparison with the incisions 228, 232 shown on the left breast, both the first incision 228 and the second incision 232 are positioned beneath the manifold layer 204 shown in FIG. 9. The manifold layer 204 has not yet been curved to conform to the breast, so the scores of the scoring pattern 208 are narrow.

FIG. 10 illustrates the wound dressing 100 secured to a surface defined by the woman's left breast. The inset shows the manifold layer 204. The first lobe 160'' covers a lower portion of the breast area and is curved around the ribcage to cover a portion of a left side of the torso proximate the left armpit. The second lobe 168'' covers an upper portion of the breast area. The manifold layer 204 has been curved to conform to the shape of the breast, and the scores of the scoring pattern 208 have splayed apart to conform to the curvature of the breast. The point 174'' is positioned proximate a bottom of the sternum.

Due to the symmetric shape of the manifold layer 204, the manifold layer 204 can be used to treat wounds in both the left breast (FIG. 10) and the right breast (FIG. 9) without requiring modification. As can best be seen in FIG. 10, the wound dressing 100 is sized so that a wound dressing 100 can simultaneously be used independently treat each breast.

Wound Dressing

Figure 11:
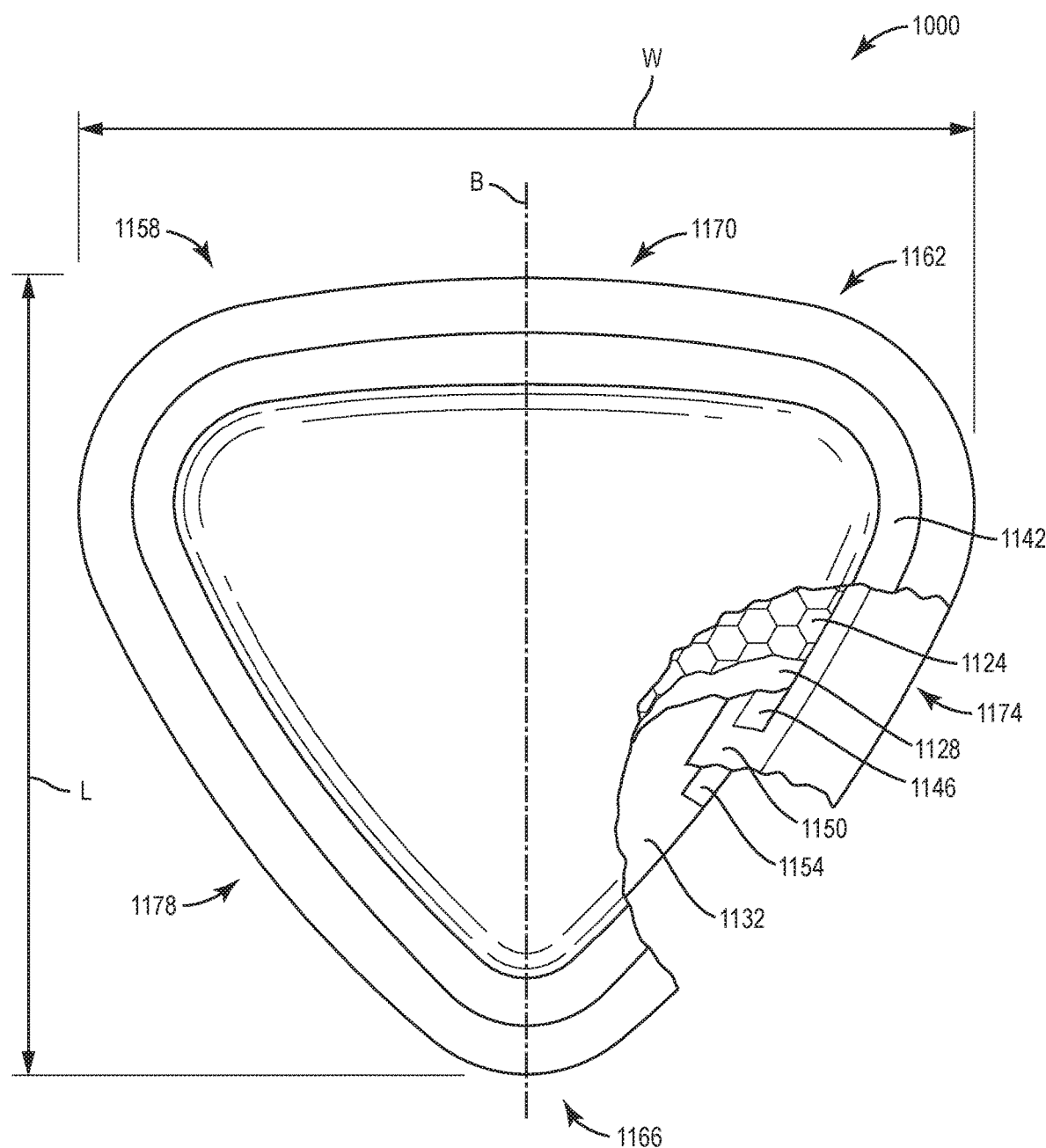
FIG. 11 is a front view of a wound dressing according to an exemplary embodiment.

FIG. 11 illustrates a wound dressing 1000 having a single lobe according to an exemplary embodiment. The wound dressing 1000 is substantially similar to the wound dressing 100. Like parts between the wound dressings 100 and 1000 are indicated by preceding corresponding parts of the wound dressing 100 with the number 1. The wound dressing 100 has a profile or a perimeter that is generally shaped like a guitar pick (e.g., generally triangular and having curved sides and corners). It is contemplated that the size of the wound dressing 1000 can range from 180 cm² to 1000 cm². More preferably, the size of the wound dressing 1000 can range from 370 cm² to 380 cm².

The wound dressing 1000 is shown to include a plurality of layers, including a drape layer 1120, a manifold layer 1124, a wound-interface layer 1128, a rigid support layer 1142, a first adhesive layer 1146, and a second adhesive layer 1150. In some embodiments, the wound dressing 1000 includes a removable cover sheet to cover the manifold layer 1124, the wound-interface layer 128, the second adhesive layer 1150, and/or the patient contacting layer 1154 before use.

Manifold layer

Referring to FIG. 11, the manifold layer 1124 includes a first surface and a second, wound-facing surface opposite the first surface. When the wound dressing 1000 is applied to a wound, the first surface faces away from the wound, whereas the second surface faces toward the wound. As described above, the manifold layer 1124 can be made from a porous and permeable foam-like material and, more particularly, a reticulated, open-cell polyurethane or polyether foam that allows good permeability of wound fluids while under a reduced pressure. One such foam material that has been used is the VAC® Granufoam™ material that is available from Kinetic Concepts, Inc. (KCI) of San Antonio, Tex. Any material or combination of materials might be used for the manifold layer 1124 provided that the manifold layer 1124 is operable to distribute the reduced pressure and provide a distributed compressive force along the wound site.

As shown in FIG. 11, the manifold layer 1124 is generally symmetrical and forms defines a single lobe that is generally shaped like a guitar pick (e.g., generally triangular and having curved sides and corners). The manifold layer 1124 includes a first curved corner 1158, a second curved corner 1162, and a third curved corner 1166. A first side 1170 extends between the first curved corner 1158 and the third curved corner 1166, a second side 1174 extends between the second curved corner 1162 and the third curved corner 1166, and a third side 1178 extends between the first curved corner 1158 and the second curved corner 1162. The manifold layer 1124 can have a width W ranging between 8 cm and 40 cm, and more preferably between 17 cm and 33 cm. The manifold layer 1124 can have a length L ranging between 7 cm and 35 cm, and more preferably between 14 cm and 30 cm. The manifold layer 1124 can have a thickness T ranging between 14 mm and 24 mm, and more preferably 19 mm. Each of the sides 1170, 1174, 1178 is generally convex and has a radius of curvature of approximately 42.3 cm. The first curved corner 1158 and the second curved corner 1162 are less curved than the third curved corner 1166. More specifically, the first curved corner 1158, the second curved corner 1162, and the third curved corner 1166 can each have a radius of curvature ranging between 3 cm and 10 cm. More preferably, the first curved corner 1158 and the second curved corner 1162 can each have a radius of curvature of approximately 4.8 cm. More preferably, the third curved corner 1166 can have a radius of curvature of approximately 3.5 cm. In the illustrated embodiment, the wound dressing 1000 is generally symmetric about the axis B.

The manifold layer 1124 can have any of the scoring patterns 176, 184, 208, 216 described above. The manifold layer 1124 can be used in a wound therapy system similar to the wound therapy system described below and illustrated in FIG. 4.

The wound dressing 1000 can be positioned relative to a woman's torso in a manner similar to what is illustrated in FIGS. 9 and 10 for the wound dressing 100 and the manifold layer 204. The wound dressing 1000 is sized to cover the surface including the entire breast area, including the first incision 228, the second incision 232, and any incisions proximate the armpit as described above. More specifically, the third side 1178, extending between the first curved corner 1158 and the second curved corner 1162, is positioned proximate the patient's armpit and the third curved corner 1166 is oriented towards a bottom portion of the patient's sternum. Due to the symmetric shape of the wound dressing 1000, the wound dressing 1000 can be used to treat wounds in both the left breast and the right breast without requiring modification. For example, when the wound dressing 1000 is oriented to treat the right breast in a manner similar to what is illustrated with respect to the manifold layer 204 in FIG. 9, the second side 1174, which extends between the second curved corner 1162 and the third curved corner 1166, covers an upper portion of the breast area and the first side 1170, which extends between the first curved corner 1158 and the third curved corner 1166, covers a lower portion of the breast area. When the wound dressing 1000 is oriented to treat the left breast in a manner similar to what is illustrated with respect to the wound dressing 100 and the manifold layer 204 in FIG. 10, the first side 1170, which extends between the first curved corner 1158 and the third curved corner 1166, covers an upper portion of the breast area and the second side 1174, which extends between the second curved corner 1162 and the third curved corner 1166, covers a lower portion of the breast area.

Wound Therapy System

Referring now to FIG. 4, a wound therapy system 236 is shown engaged with the surface 104 of a patient to treat a region proximate an incision 240, according to an exemplary embodiment. The incision 240 extends through the epidermis 244, or skin, and dermis 248, and reaches into a hypodermis 252, or subcutaneous tissue. The subcutaneous tissue 252 may include breast tissue, fatty tissue, or muscle. An undermined subcutaneous tissue site 252 is shown extending from the incision 240, and in the illustrated embodiment, shows a subcutaneous defect or void 256 that may be caused by surgical procedures, such as full or partial mastectomies, breast enhancements, and/or breast reductions. The incision 240 can be closed using any closing device such as sutures, staples, or an adhesive. In the illustrated embodiment, the incision 240 is closed using a suture 260.

The wound therapy system 236 further includes a removed fluid container 272 and a negative pressure source or pump 276 that are in fluid communication with the wound dressing 100 via the removed fluid conduit 268. The removed fluid container 272 can be configured to store a fluid removed from incision 240. Removed fluid can include, for example, wound exudate (e.g., bodily fluids), air, or any other type of fluid which can be removed from the incision 240 during wound treatment.

With continued reference to FIG. 4, the wound dressing 100 is positioned above the incision 240. The second adhesive layer 150 secures the wound dressing 100 to the patient. The wound-interface layer 128 contacts the surface 104 of the patient, and the manifold layer 204 is positioned above the wound-interface layer 128. The drape layer 120 extends over the manifold layer 204 to provide a fluid-tight seal of the wound dressing 100. The reduced-pressure interface 158 is engaged with an L-shaped connector 264 configured to engage a removed fluid conduit 268. In the illustrated embodiment, the removed fluid conduit 268 is a multi-lumen conduit. The removed fluid conduit 268 includes a first lumen 274 and a second lumen 278. The first lumen 274 is configured to apply negative pressure to the wound dressing 100 and to draw exudate into the removed fluid container 272. The second lumen 278 is configured for sensing the pressure of the wound dressing 100. One such wound therapy system 236 including a multi-lumen conduit is the SensaT.R.A.C.™ system that is available from Kinetic Concepts, Inc. (KCI) of San Antonio, Tex.

Negative Pressure Wound Treatment Therapy

FIG. 10 illustrates a NPWT system engaged with the wound dressing 100. The NPWT system includes the pump 276 configured to apply a negative pressure to the wound site and the removed fluid container 272 to retain exudate from the wound site. In addition to providing NPWT, the negative pressure caused by the pump 276 provides support to the breast tissue. The compressive forces caused by the negative pressure hold any remaining breast tissue, reconstructive material, and/or implant material in position as the wound heals.

In embodiments in which both breasts are treated using the wound dressings 100, the wound dressings 100 may be connected to different pumps or the wound dressings 100 may be connected to the same pump 276 using a Y connector (not shown). In either configuration, the use of separate wound dressings on each breast allows the NPWT to be customized for each breast. For example, breasts having different sizes of wounds or wounds healing at different rates can have different NPWT requirements. Accordingly, the use of separate wound dressings 100 on each breast allows the treatment protocol for each wound to be customized.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

What is claimed is:

1. A negative pressure wound dressing for use with breast incisions, the wound dressing comprising:
a drape layer having a first surface and a second, wound-facing surface, wherein the drape layer is substantially impermeable to liquid and substantially permeable to vapor;
a manifold layer having a first surface and a second, wound-facing surface, the manifold layer having a perimeter defined by a first convex curved corner side surface having a first radius of curvature defining a first lobe, a second convex curved corner side surface having a second radius of curvature defining a second lobe, and a concave connecting portion between the first lobe and the second lobe;
a wound-interface layer having a first surface and a second, wound-facing surface, the second, wound-facing surface of the wound-interface layer configured to directly contact a surface of a patient's tissue;
a base layer configured to secure the drape layer to the manifold layer and the wound-interface layer, and configured to secure the wound dressing to the patient's tissue, the base layer comprising:
a first adhesive layer having a first surface and a second, wound-facing surface, the first surface of the first adhesive layer configured to be coupled to a perimeter of the second surface of the wound-interface layer,
a second adhesive layer having a first surface and a second, wound-facing surface, the first surface of the second adhesive layer configured to be coupled to a perimeter of the first adhesive layer and the perimeter of the drape layer, and
a patient-contacting layer having a first surface and a second, wound-facing surface, the first surface of the patient-contacting layer configured to be coupled to a perimeter of the second surface of the second adhesive and at least a portion of the second surface of the patient-contacting layer configured to be coupled to the patient's tissue; and
a reduced-pressure interface integrated with the drape layer.

2. The wound dressing of claim 1, wherein the wound-interface layer comprises a wicking material.

3. The wound dressing of claim 1, wherein the reduced-pressure interface is fluidly coupled to a multi-lumen fluid conduit.

4. The wound dressing of claim 3, further comprising a negative pressure device coupled to the multi-lumen fluid conduit such that the reduced-pressure interface is in fluid communication with the negative pressure device.

5. The wound dressing of claim 1, wherein the first lobe and the second lobe have a radius of curvature within the range of 3 cm to 10 cm.

6. The wound dressing of claim 1, wherein the first surface of the manifold layer includes a scoring pattern having a plurality of scores formed therein and the manifold layer is configured to bend about at least one of the scores of the scoring pattern.

7. The wound dressing of claim 1, wherein one of the first lobe and the second lobe is configured to conform to a shape of an upper portion of a breast and the other of the first lobe and the second lobe is configured to conform to a shape of a lower portion of a breast.

8. The wound dressing of claim 1, further comprising a cover sheet configured to be removably coupled to the base layer.

9. A negative pressure wound dressing for use with breast incisions, the wound dressing comprising:
a drape layer having a first surface and a second, wound-facing surface, wherein the drape layer is substantially impermeable to liquid and substantially permeable to vapor;
a manifold layer having a first surface and a second, wound-facing surface, the manifold layer including a perimeter defined by a first curved corner, a second curved corner, and a third curved corner, wherein a first side extends between the first curved corner and the third curved corner, a second side extends between the second curved corner and the third curved corner, and a third side extends between the first curved corner and the second curved corner;

wherein the first surface of the manifold layer includes a scoring pattern having a plurality of scores formed therein, the manifold layer configured to bend about at least one of the scores of the scoring pattern;

a wound-interface layer having a first surface and a second, wound-facing surface, the second, wound-facing surface of the wound-interface layer configured to directly contact a surface of a patient's tissue;

a base layer configured to secure the drape layer to the manifold layer and the wound-interface layer, and configured to secure the dressing to the patient's tissue, the base layer comprising:

a first adhesive layer having a first surface and a second, wound-facing surface, the first surface of the first adhesive layer configured to be coupled to a perimeter of the second surface of the wound-interface layer, a second adhesive layer having a first surface and a second, wound-facing surface, the first surface of the second adhesive layer configured to be coupled to a perimeter of the first adhesive layer and the perimeter of the drape layer, and a patient-contacting layer having a first surface and a second, wound-facing surface, the first surface of the patient-contacting layer configured to be coupled to a perimeter of the second surface of the second adhesive and at least a portion of the second surface of the patient-contacting layer configured to be coupled to the patient's tissue; and a reduced-pressure interface integrated with the drape layer.

10. The wound dressing of claim 9, wherein the wound-interface layer comprises a wicking material.

11. The wound dressing of claim 9, wherein the reduced-pressure interface is fluidly coupled to a multi-lumen fluid conduit.

12. The wound dressing of claim 11, further comprising a negative pressure device coupled to the multi-lumen fluid conduit such that the reduced-pressure interface is in fluid communication with the negative pressure device.

13. The wound dressing of claim 9, wherein the first curved corner, the second curved corner, and the third curved corner have a radius of curvature within the range of 3 cm to 10 cm, and wherein the first curved corner and the second curved corner have a radius of curvature larger than the third curved corner.

14. The wound dressing of claim 9, wherein one of the first side and the second side is configured to conform to a shape of an upper portion of a breast and the other of the first side and the second side is configured to conform to a shape of a lower portion of a breast.

* * * * *